United States Patent [19]

Nollan

[11] 4,127,113

[45] Nov. 28, 1978

[54] MULTIPLE SMEAR BRUSH

[75] Inventor: Theodore G. Nollan, Chula Vista, Calif.

[73] Assignee: Pap Smear Center, Inc., San Diego, Calif.

[21] Appl. No.: 860,881

[22] Filed: Dec. 15, 1977

[51] Int. Cl.² .............................................. A61B 10/00
[52] U.S. Cl. .................................... 128/2 W; 15/201; 128/2 B; 128/357
[58] Field of Search .............. 128/2 B, 2 W, 304, 357; 15/201

[56] References Cited

U.S. PATENT DOCUMENTS

| | | | |
|---|---|---|---|
| 1,520,908 | 12/1924 | Meyer | 128/357 |
| 2,839,049 | 6/1958 | MacLean | 128/2 B |
| 2,955,591 | 10/1960 | MacLean | 128/2 B |
| 3,088,454 | 5/1963 | Shute | 128/2 B |
| 3,633,565 | 1/1972 | McDonald | 128/2 B |
| 3,796,211 | 3/1974 | Kohl | 128/2 B |
| 3,881,464 | 5/1975 | Levene | 128/2 B |
| 4,016,865 | 4/1977 | Fredericks | 128/2 B |

FOREIGN PATENT DOCUMENTS

| | | | |
|---|---|---|---|
| 604,145 | 10/1934 | Fed. Rep. of Germany | 128/357 |
| 304,020 | 1/1929 | United Kingdom | 128/357 |

*Primary Examiner*—Kyle L. Howell
*Attorney, Agent, or Firm*—Brown & Martin

[57] ABSTRACT

A smear brush for obtaining cellular samples from a body cavity. The instrument has a rigid stem with a handle at one end, the other end having an integral brush with a flexible spine and fine flexible bristles. A flat blade at the root of the spines serves as a locator and stop at the entrance to a body cavity, while the flexible brush penetrates the cavity and follows any curvature of the cavity. When the instrument is rotated the brush accumulates sample material from substantially the entire inner wall of the cavity, the brush being subsequently wiped across a slide to deposit the sample for examination.

5 Claims, 6 Drawing Figures

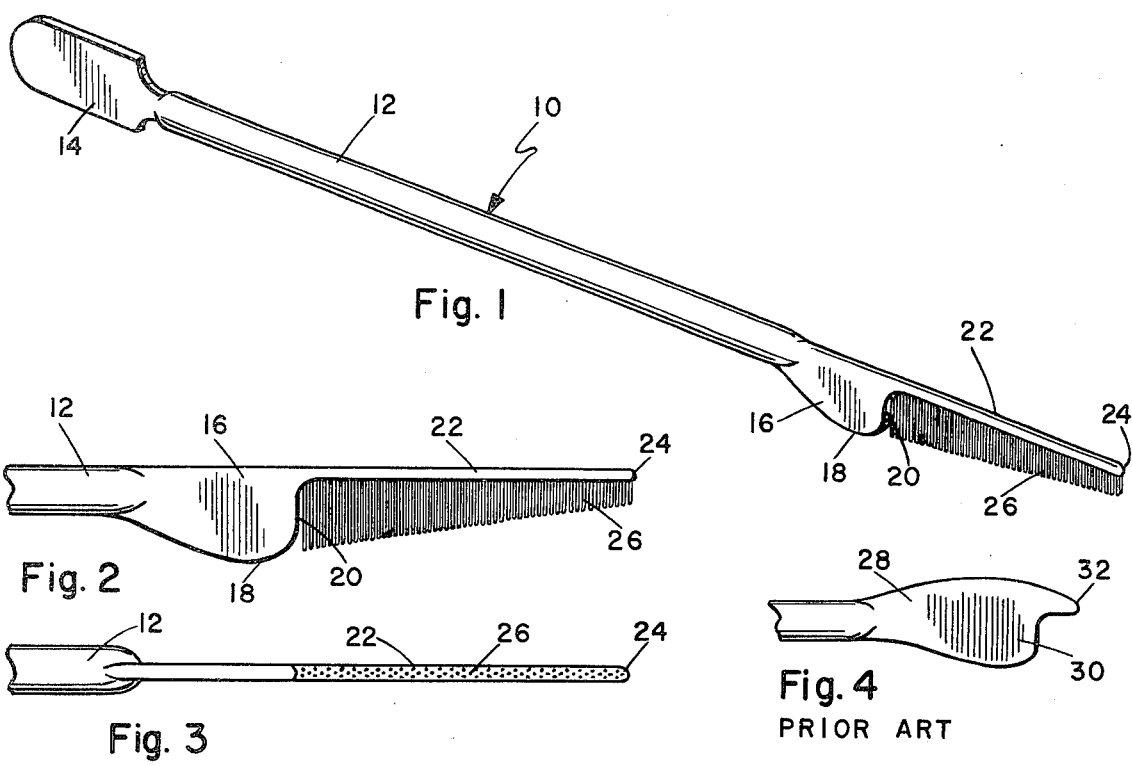
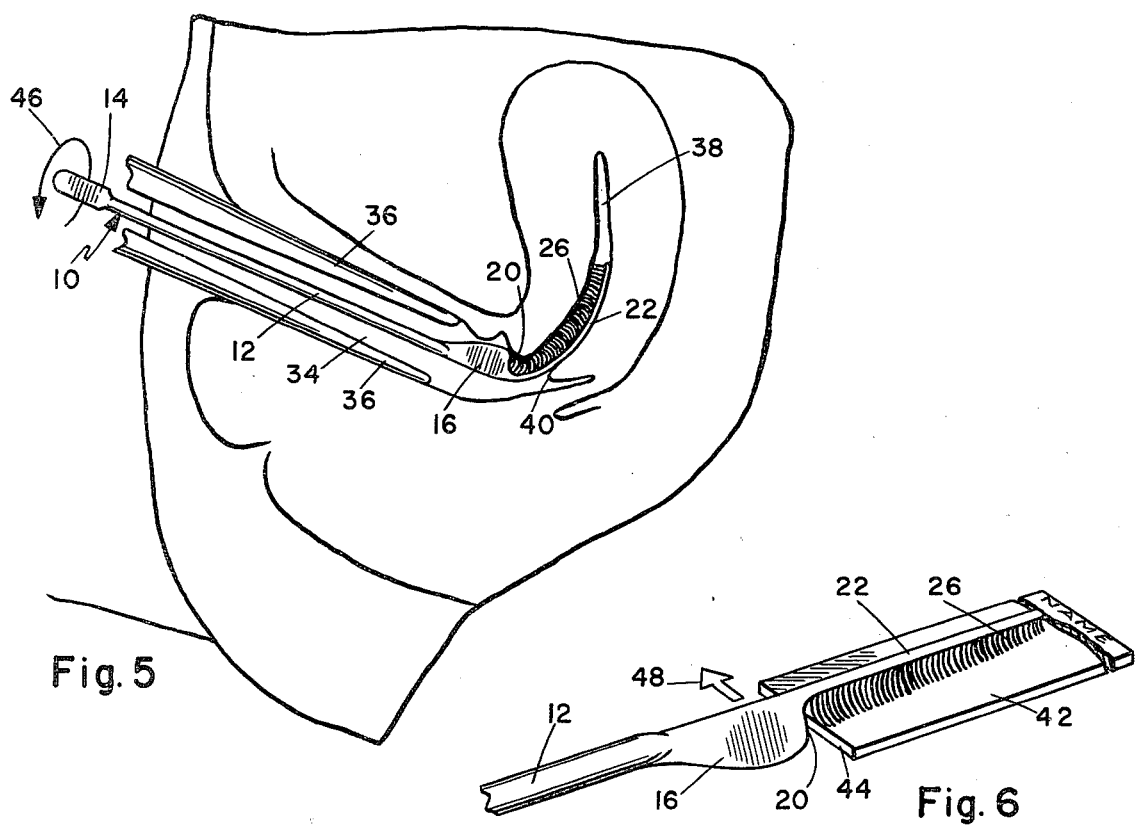

4,127,113

MULTIPLE SMEAR BRUSH

BACKGROUND OF THE INVENTION

Many different instruments have been devised for obtaining diagnostic samples from various cavities of the body. In the routine pap smear check for cancer, the most commonly used instrument has an elongaged stem with a shaped flat blade at one end. The instrument is inserted to place the blade at the cervical opening and is then rotated to scrape off cellular material, which is deposited on a microscope slide for examination.

This technique is effective only when there is desquamation of the pertinent cellular material at the cervical opening. If no suspect cells are discovered there is normally no further testing. However, there may be significant samples in the endocervix and on the endometrium which are not reached by the blade type instrument. A diagnosis based on the samples obtained by the conventional blade type instrument may therefore be incomplete and it may be possible that a malignancy or other dangerous condition exists, yet remains undetected. Since the consequences of an undetected malignancy can be very serious particularly with the possibility of cancer, it is very desirable to obtain a more complete sample that is normally obtained in the standard pap smear test.

SUMMARY OF THE INVENTION

The sample collecting instrument described herein is capable of obtaining comprehensive samples of material from deep inside body cavities and is especially adaptable to the pap smear test for cancer. The instrument has an elongated rigid stem with a handle at one end to facilitate manipulation. At the other end is a brush with a thin flexible spine integral with and extending from the rigid stem. Along the spine is a row of fine flexible bristles, the length of the bristles along the row being tapered. At the root of the spine the bristles are longest and become shorter towards the tip. Also at the root of the brush is a flat blade which serves as a positioning and stop element at the cervical opening while the brush enters the cervical canal. The instrument can readily be made as a unitary structure, such as by injection molding from plastic, and at the low cost necessary for an expendable item.

The flexibility of the brush allows it to follow the curvature of the cervical canal to ensure proper contact. When the instrument is rotated 360°, the brush gathers benign, atypical, dysplastic or malignant cells from the endocervix and endometrium that are normally inaccessible to the usual scraper type instrument. The sampling does not therefore depend on spontaneous desquamation of atypical cells at the cervical opening, but obtains a large sample from deep in the cavity.

The sample is readily transferred to a slide by wiping the brush across the slide, using the flat blade as a guide on the end edge of the slide. If atypical cells are detected, in the examination, a follow up study can then be made, with aspiration of the endocervix and endometrium to determine the location of the lesion. By greatly improving the efficiency of the pap smear test by this technique, it will be possible to provide early detection of cancer in many cases which would otherwise go undetected, resulting in a decrease in the mortality rate.

The primary object of this invention, therefore, is to provide a new and improved smear brush.

Another object of this invention is to provide a smear brush having a flexible brush portion to conform to the contours of a body cavity.

Another object of this invention is to provide a smear brush which is used according to a well known technique but produces superior results.

A further object of this invention is to provide a smear brush which can be economically manufactured as a unitary element ready for immediate use.

Other objects and advantages will be apparent in the following detailed description, taken in conjunction with the accompanying drawing, in which:

FIG. 1 is a perspective view of the smear brush.

FIG. 2 is an enlarged side elevation view of the brush portion.

FIG. 3 is a bottom plan view of the brush portion.

FIG. 4 is a side elevation view of the prior art scraper instrument.

FIG. 5 illustrates a typical use of the smear brush.

FIG. 6 illustrates the transfer of a smear sample to a slide.

DESCRIPTION OF THE PREFERRED EMBODIMENT

The instrument 10 comprises an elongated rigid stem 12, having a flattened handle 14 at one end to facilitate manipulation. At the other end of stem 12 is a flattened blade 16 projecting to one side, with a smoothly rounded edge 18 and an end wall 20 substantially perpendicular to the stem. Blade 16 blends smoothly into a thin elongated spine 22 extending from the stem, the spine having a rounded tip 24 to prevent injury to the lining of the body cavity. Along the length of the spine 22 are fine bristles 26, preferably in staggered rows and coplanar with blade 16. The bristles 26 are tapered in length along the spine and are longest at the root adjacent to the blade 16, tapering linearly to about half that length at the tip 24.

The instrument is preferably made in one piece, such as by injection molding from plastic. Other means of manufacture may be used, but low cost is an important factor since the instrument is normally discarded after a single use.

The prior art device, shown in FIG. 4, has a similar stem and handle arrangement, but the sampling end is a scraper blade 28 having a lobe 30 extending to one side and a projecting prong 32 at the tip.

To use the instrument for a pap smear test, as illustrated in FIG. 5, the vagina 34 is distended by the blades 36 of a conventional speculum to facilitate insertion of the instrument. The brush is inserted into the cervical canal 38 until the end wall 20 stops against the cervical opening 40, or to any desired depth of insertion.

It should be noted that the length of the brush can vary, but in most instances a standard size will be satisfactory. The brush should be long enough to gather a sample over a useful length of the cavity, while avoiding trauma such as penetration of the cavity wall. As an example, a length of about 4.5 centimeters has been found adequate.

With the brush fully inserted in the cervical canal 38, the instrument is rotated 360° as indicated by arrow 46, causing the bristles 26 to wipe the endometrium around the full circumference of the canal. A cellular sample is thus collected along the full length of the brush, including the sample at the cervical opening normally picked up by a scraper type instrument. The staggered rows of bristles retain the sample as the instrument is withdrawn.

To transfer the sample to a microscope slide 42, as in FIG. 6, the full length of the brush is wiped across the width of the slide as indicated by arrow 48, using end wall 20 as a guide against the end edge 44 of the slide. The bristles 26 trail and deposit the sample material as a film across the slide. The smear should be made immediately after the sample is taken, after which cell fixation must be applied in the usual manner to avoid drying effect and the rapid degeneration of the fragile columnar cells in the sample. After fixation is complete the smear can be stained with the standard Popanicolaov staining technique to make the cells readily visible. The slide can then be studied in the usual manner to detect atypical cells which would warrant further tests or treatment. Since the entire length of the brush is wiped across the slide, the location of a suspect cell or cells along the length of the slide will indicate the approximate location of the lesion in the cervical canal. This will facilitate subsequent examination and tests.

Since the pap smear test, used herein as the primary example, is widely conducted and is considered to be very useful in the early detection of cancer, any improvement in the reliability of the initial diagnosis can be very important. The smear brush provides a great improvement over the usual mass examination technique using the wooden or plastic cervical scrapers, yet is as simple to use as the scraper instrument. The more reliable examination can thus be conducted without significant or costly changes in technique.

Having described my invention, I claim:

1. A multiple smear brush, comprising:
    an elongated, substantially rigid stem having an enlarged handle at one end;
    a brush at the other end of said stem, said brush including a thin flexible spine projecting from the stem and having a root end at the stem and a smoothly rounded tip;
    and a longitudinal planar row of thin flexible bristles projecting from one side of said spine.

2. A multiple smear brush according to claim 1, wherein said bristles taper in length from a maximum at said root end to a minimum at said tip.

3. A multiple smear brush according to claim 2, wherein said bristles taper linearly from root end to tip.

4. A multiple smear brush according to claim 1, and including a flat blade projecting from said stem adjacent the junction with said spine and being coplanar with said bristles.

5. A multiple smear brush according to claim 4, wherein said blade has an end wall substantially perpendicular to the spine adjacent the root end of said bristles, and a smoothly rounded edge blending into said spoine and said stem.

* * * * *

UNITED STATES PATENT AND TRADEMARK OFFICE
CERTIFICATE OF CORRECTION

PATENT NO. : 4,127,113
DATED : November 28, 1978
INVENTOR(S) : Theodore G. Nollan It is certified that error appears in the above-identified patent and that said Letters Patent are hereby corrected as shown below:

Column 1, line 26, "that" should be --than--.

Column 3, line 13, "Popanicolaov" should be --Papanicolaou--.

Column 4, line 26, in Claim 5, "spoine" should be --spline--.

Signed and Sealed this

Twenty-fourth Day of April 1979

[SEAL]

Attest:

RUTH C. MASON
Attesting Officer

DONALD W. BANNER
Commissioner of Patents and Trademarks